(12) United States Patent
Fabricius et al.

(10) Patent No.: US 7,170,823 B2
(45) Date of Patent: Jan. 30, 2007

(54) MEDICAL DISPENSER, A BLISTER CARD FOR USE IN THE DISPENSER AND A METHOD OF DISPENSING MEDICAL DOSES

(75) Inventors: Paul Erik Fabricius, Holstebro (DK); Niels Toft Jørgensen, Løsning (DK)

(73) Assignee: Bang & Olufsen Medicom A/S, Struer (DE)

( * ) Notice: Subject to any disclaimer, the term of this patent is extended or adjusted under 35 U.S.C. 154(b) by 74 days.

(21) Appl. No.: 10/934,560

(22) Filed: Sep. 7, 2004

(65) Prior Publication Data

US 2005/0087473 A1 Apr. 28, 2005

Related U.S. Application Data

(63) Continuation of application No. PCT/DK03/00142, filed on Mar. 6, 2003.

(30) Foreign Application Priority Data

Mar. 7, 2002 (DK) ............... 2002 00352
Sep. 16, 2002 (DK) ............... 2002 01365

(51) Int. Cl.
G04B 47/00 (2006.01)
B65D 83/04 (2006.01)
G06F 17/00 (2006.01)
G07F 11/00 (2006.01)

(52) U.S. Cl. ............ 368/10; 206/534.1; 221/2; 700/242

(58) Field of Classification Search .......... 368/10; 206/534.1, 534.2; 221/2, 3, 15; 700/236, 700/242

See application file for complete search history.

(56) References Cited

U.S. PATENT DOCUMENTS 4,588,303 A 5/1986 Wirtschafter et al.

(Continued)

FOREIGN PATENT DOCUMENTS

FR 2611671 9/1988

(Continued)

*Primary Examiner*—Vit W. Miska
(74) *Attorney, Agent, or Firm*—Harness, Dickey & Pierce P.L.C.

(57) ABSTRACT

A medical dispenser being adapted to hold a number of medical doses and being adapted to determine when a user or patient gains access to one or more of the medical doses, the dispenser comprising: means for determining each of a first plurality of points in time or time intervals at which the user or patient should take a medical dose, means for detecting each of a second plurality of points in time where the user or patient gained access to the medical doses, means for providing to the user or patient information relating to a relation between the first and second pluralities, and wherein the providing means are adapted to, if the user gains access to the medication multiple times per point in time or time interval in the first plurality of points in time or time intervals, provide information relating to a relation between the pairs of one of the firs plurality of points in time or time intervals and a first of the second plurality of points in time occurring after the pertaining point in time of the first plurality or within time interval of the first plurality.

10 Claims, 8 Drawing Sheets

U.S. PATENT DOCUMENTS

| | | |
|---|---|---|
| 4,660,991 A | 4/1987 | Simon |
| 4,725,997 A | 2/1988 | Urquhart et al. |
| 4,748,600 A | 5/1988 | Urquhart |
| 5,020,037 A | 5/1991 | Raven |
| 5,072,430 A | 12/1991 | Eckernäs et al. |
| 5,200,891 A | 4/1993 | Kehr et al. |
| 5,289,157 A | 2/1994 | Rudick et al. |
| 5,593,390 A | 1/1997 | Castellano et al. |
| 5,805,051 A * | 9/1998 | Herrmann et al. ....... 340/309.4 |
| 5,826,217 A * | 10/1998 | Lerner ........................ 702/177 |
| 6,075,755 A | 6/2000 | Zarchan |
| 6,335,907 B1 * | 1/2002 | Momich et al. ............... 368/10 |
| 6,529,446 B1 * | 3/2003 | de la Huerga ................ 368/10 |

FOREIGN PATENT DOCUMENTS

| | | |
|---|---|---|
| FR | 2787317 | 6/2000 |
| WO | WO98/42591 | 10/1998 |
| WO | WO 99/43283 | 9/1999 |
| WO | WO 00/25720 | 5/2000 |
| WO | WO 01/08106 A2 | 2/2001 |
| WO | WO 02/24141 A1 | 3/2002 |
| WO | WO 03/003970 A1 | 1/2003 |

* cited by examiner

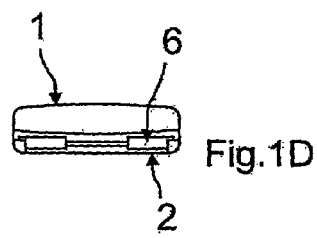
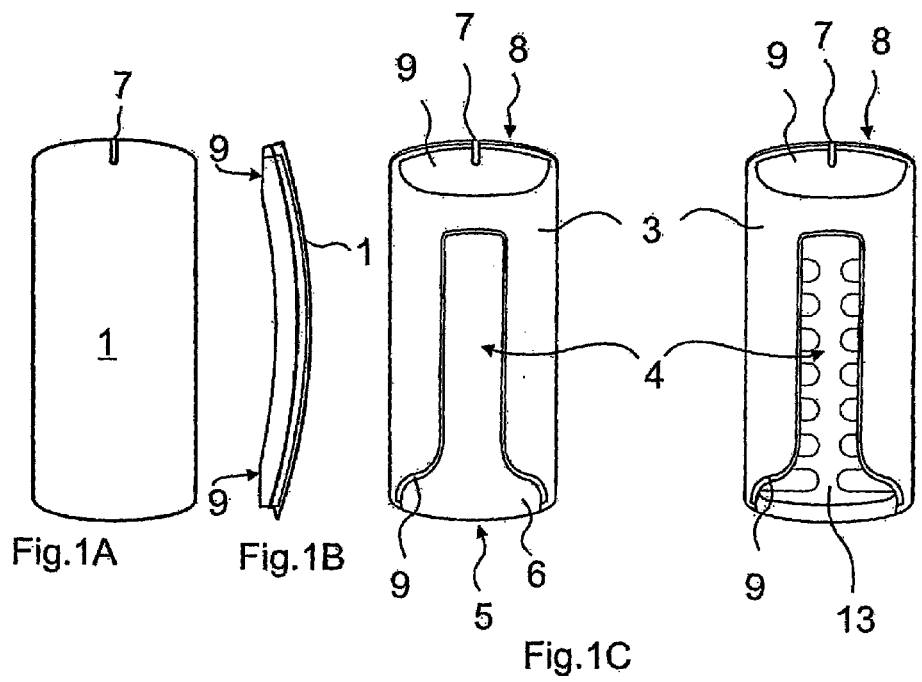
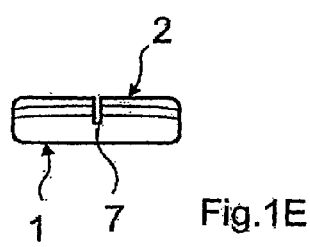

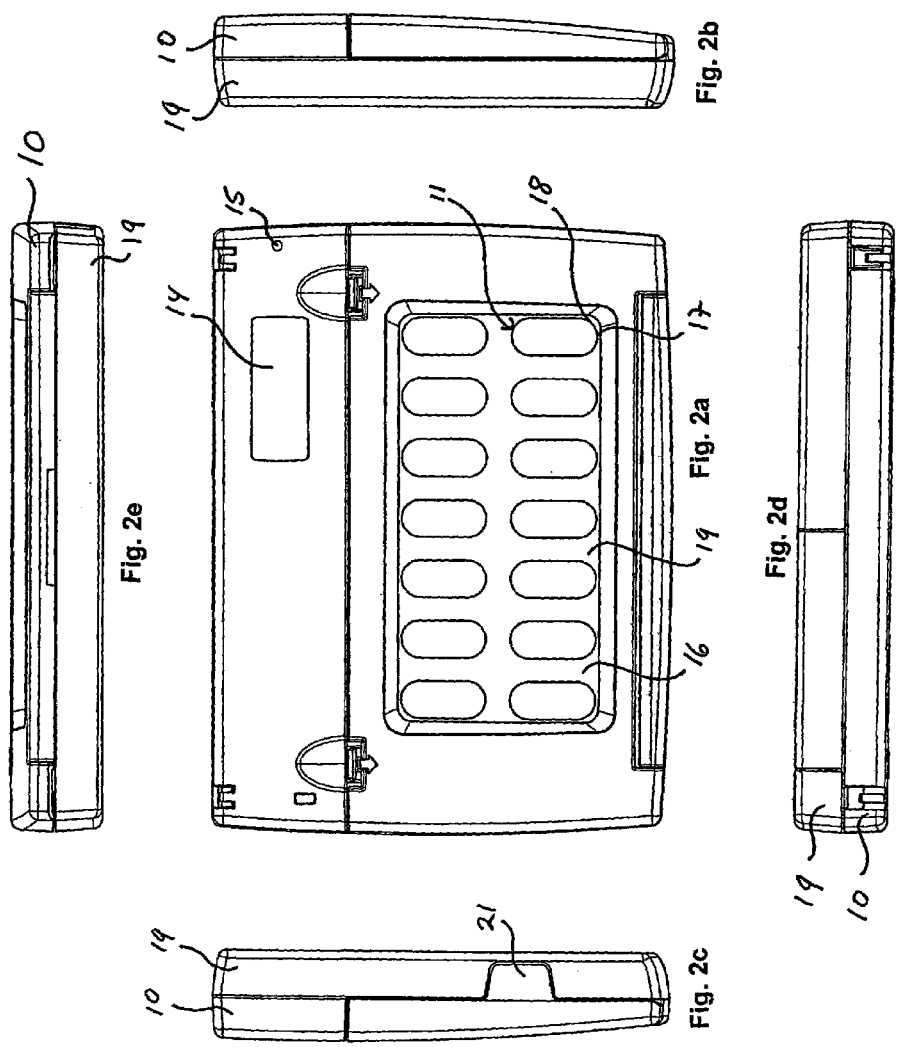

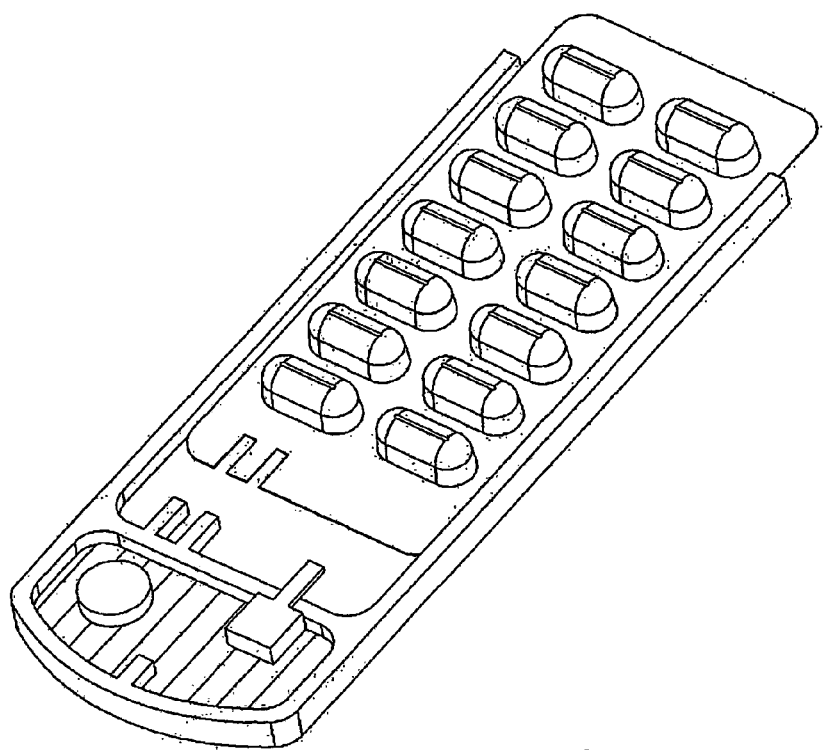
Fig. 3a
Fig. 3b
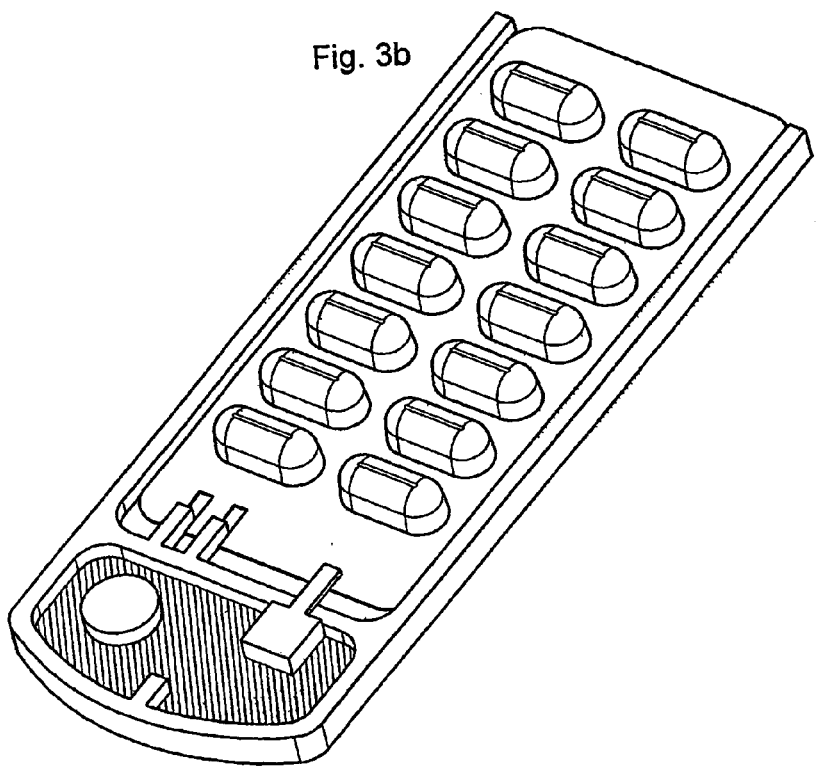

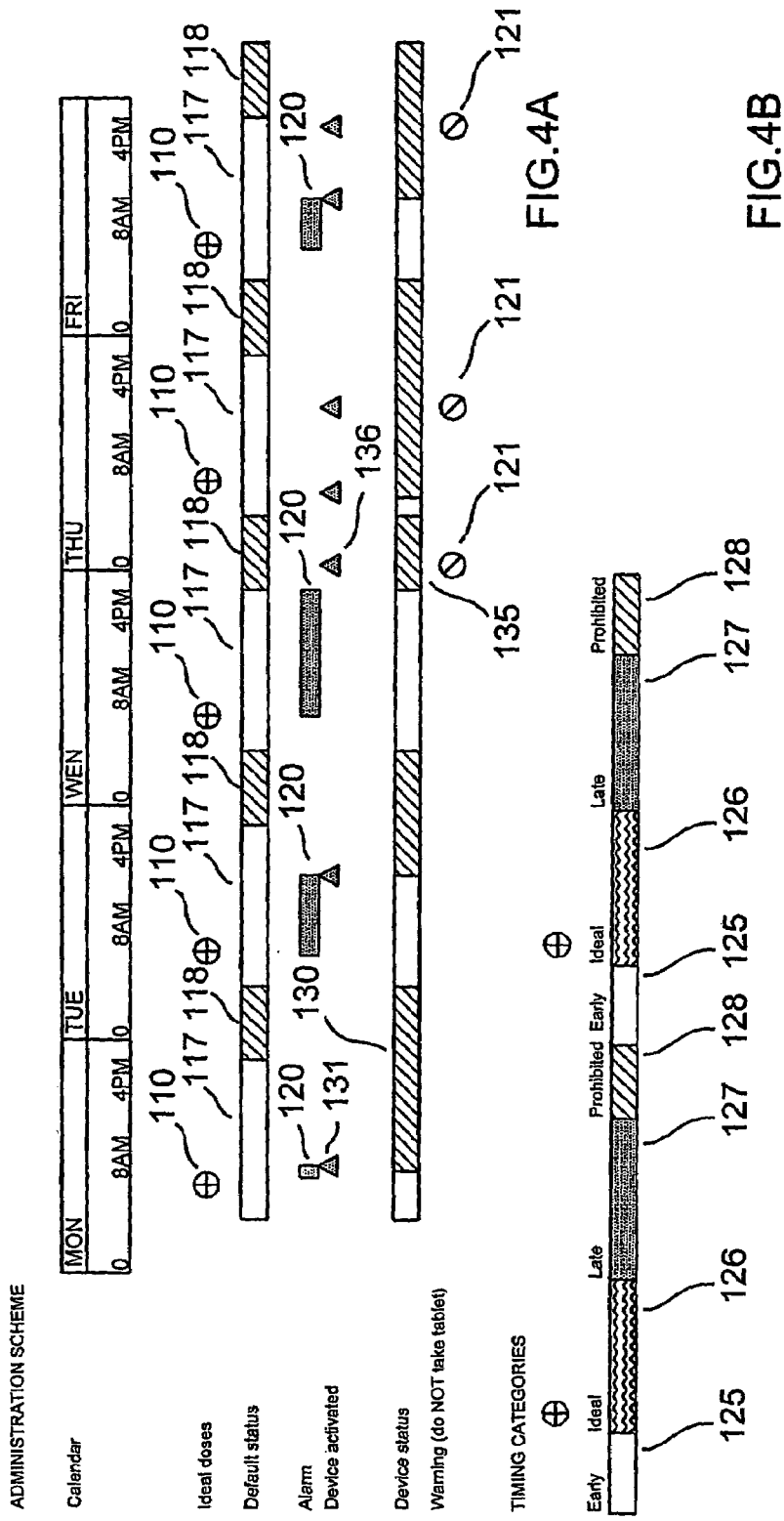

MEDICAL DISPENSER, A BLISTER CARD FOR USE IN THE DISPENSER AND A METHOD OF DISPENSING MEDICAL DOSES

This application is a continuation of, and claims priority under 35 U.S.C. §120 and 35 U.S.C. §365(c) from, PCT International Application No. PCT/DK03/00142 International filing date of Mar. 6, 2003, which designated the United States of America, which further claims priority on DANISH Application Priority Number PA 2002 00352 filed Mar. 7, 2002, and DANISH Application Priority Number PA 2002 01365 filed Sep. 16, 2002, the entire contents of each of which are hereby incorporated herein by reference.

The present invention relates to a medical dispenser which may be able to determine when a user gains access to medical doses held thereby and which may be able to inform the user of when to take one or more medical doses or how the user conforms to a medication schedule. In addition, the invention relates to a blister card for use in the dispenser, the blister card providing a novel feature in that it may inform the dispenser of certain functionalities and situations, and the user may inform the dispenser of certain selections via the blister card.

Intelligent dispensers are heavily researched these days in that they may unload the public service functions (doctors, hospitals, other caretakers) as well as prevent or reduce wrongful medication.

Such dispensers may be seen in WO00/25720, FR2 787 317, WO98/42591, U.S. Pat. No. 4,660,991, and WO02/24141.

Most of these intelligent dispensers aim to overtake the full responsibility for the providing of the medication and are aimed at weak patients that tend to forget their medication or take wrong doses at the wrong times.

The present invention aims at stronger patients that only need to be reminded to take the medication or who need to be reminded of how closely they follow a given medication schedule.

In a first aspect, the invention relates to a medical dispenser being adapted to hold a number of medical doses and being adapted to determine when a user or patient gains access to one or more of the medical doses, the dispenser comprising:
 means for determining each of a first plurality of points in time or time intervals at which the user or patient should take a medical dose,
 means for detecting each of a second plurality of points in time where the user or patient gained access to the medical doses, and
 means for providing to the user or patient information relating to a relation between the first and second pluralities.

In the present context, the dispenser holds the medical doses but does not necessarily dispense only a single dose to the user or patient. The access of the user may be to all doses in the dispenser, whereby the user will then dispense the dose(s) required himself.

In the present context, "gains access to" means that the dispenser is able to determine when the user has the ability to take a dose of medication. This does not necessarily mean that the user actually takes the medication. This rather simple dispenser needs not have means for preventing the user from gaining access to the medication, but it will detect that access.

Normally, when determining a medication schedule for a user or patient, the medication should preferably be given with fixed time intervals in order to control the concentration of the medicine in the users body. Thus, in order to obtain that, preferred times or time intervals (usually starting at or shortly before the preferred time of intake of the medication) are normally set for the actual medication and the person in question.

In the present context, the user should preferably (taking into account the optimal function of the medication) take the medicine at the points in time or within the time intervals. However, as is described above, the present dispenser needs not ascertain that the user in fact does take the medication.

Knowing when the medication should have been taken and when the medication was (presumably) taken, a relation between those periods of time may be made in order to have a measure of how well the user conforms to the medication schedule.

Preferably, the first and second pluralities are taken within a predetermined period of time or within a predetermined number of accesses to the medication or a predetermined number of times/intervals in the first plurality. The period of time or number of accesses/times/intervals may be varied from user to user and medication to mediation. For some medications, providing a relation over the intake of medication over a month may be desired, whereas a relation extending over only a few days may be suitable for other medications.

Preferably, the providing means are adapted to provide a relation between pairs of one of the first plurality of points in time or time intervals and one of the second plurality of points in time. A suitable manner of providing the relation is to compare pairs of an optimal time of intake and the actual (presumed) intake. In that situation, the compliance may be determined or quantified simply by the time difference between recommended intake and access to the medication.

Also, preferably, the providing means are adapted to provide a relation between the pairs of one of the first plurality of points in time or time intervals and a first of the second plurality of points in time occurring after the pertaining point in time of the first plurality or within the pertaining time interval of the first plurality. In this manner, if the user gains access to the medication (such as by accident) multiple times per point in time or time interval, only the first time the user gains access to the medication is used in the relation. Any remaining times of access are discarded. In this aspect, the dispenser may have means for warning the user, if he has already gained access to the medication once during this interval or after the last point in time for recommended intake or the dispenser may inform the user that dose intake is allowed and that the dose access is registered as a dose intake.

As mentioned, one manner of determining the relation is to have the relation relate to a time difference between the pairs of the point in time or a starting time of the time interval of the first plurality and the point in time of the second interval.

Another manner of quantifying compliance is one where the providing means are adapted to provide a relation between a number of times wherein a point in time of the second number occurs within a time interval of the first plurality, and a number of times wherein a point in time of the second number does not occur within a time interval of the first plurality. Thus, the number of times where the user actually gains access to the medication when he should are registered together with the number of times where he did not.

A number of manners exist of informing the user of the compliance. According to a first manner, the providing means are adapted to provide, as the information, one of a plurality of predetermined colours to the user, the colour being determined on the basis of the relation. Suitable colours may be red, yellow and green.

According to another manner, the providing means are adapted to provide, as the information, one of a plurality of predetermined numbers to the user, the number being determined on the basis of the relation. Suitably, the higher the number the higher the compliance.

A third manner is one wherein the providing means are adapted to activate, as the information, one or more of a plurality of predetermined areas of a display, such as a LCD display, visible to the user, the area(s) activated being determined on the basis of the relation. Such a display may illustrate a bar or pie diagram.

A fourth manner is one wherein the providing means are adapted to provide, as the information, one of a plurality of predetermined sound signals to the user, the sound signal being determined on the basis of the relation. This sound may vary from pleasant (high compliance) to unpleasant (low compliance).

Yet another manner is one wherein the providing means are adapted to provide, as the information, one of a plurality of predetermined graphical images to the user, the image being determined on the basis of the relation. Suitable images may be happy/neutral/sad face or thumb up/down.

The dispenser preferably further comprises, as described above, means for informing the user, if a point in time of the second plurality occurs outside a time interval of the first plurality in order to e.g. warn the user if he gains access to the medication outside an interval.

A second aspect of the invention relates to a medical dispenser being adapted to hold a number of medical doses and to inform a user or patient of when to take a dose, the dispenser comprising:
  means for informing the user in one of a plurality of different manners,
  means for determining a compliance of the users taking of medical doses, and
  means for selecting a manner of informing based on the determined compliance.

Thus, the dispenser may be able to inform the user differently depending on the users compliance.

Again, "when" to take a dose would normally be in accordance with a medication schedule determined either for the actual medication or set in the dispenser.

A number of different manners of informing a user are known. However, the most preferred manners are ones where the informing means are adapted to inform the user using one of sound, visual information, and/or vibration.

In that situation, the determining means may be adapted to determine a compliance selected between a predetermined number of compliances, and wherein the selecting means are adapted to select visual information based on a first compliance of the predetermined number of compliances, vibration based on a second compliance of the predetermined number of compliances, and sound based on a third compliance of the predetermined number of compliances.

Normally, especially when in a public place, visual information is the most pleasant and private information, where sound information (especially if loud) is the most unpleasant information. Thus, the dispenser may use this information manner in order to ensure that the user both takes his medication and is informed (such as by the severity of the information manner) of his compliance. This may bring the user to a better compliance in order to avoid that particular manner of informing.

Preferably, the informing means are adapted to provide the sound, visual information, or vibration with different intensities and/or frequencies.

In that manner, the determining means are preferably adapted to determine a compliance selected between a predetermined number of compliances, and wherein the selecting means are adapted to select an intensity and/or frequency based on the determined compliance. Again, the lower the compliance, the hither the frequency or intensity may be in order to ensure that the user "gets the message". The predetermined number of compliances may be the numbers of an interval (e.g. integers in the interval 0–10), a number being selected or calculated relating to the compliance.

As mentioned above, preferably, the dispenser is adapted to hold a number of medical doses and being adapted to determine when a user or patient gains access to one or more of the medical doses, the dispenser comprising:
  first means for determining each of a first plurality of points in time or time intervals at which the user or patient should take a medical dose, and
  means for detecting each of a second plurality of points in time where the user or patient gained access to the medical doses,
  wherein the compliance determining means determine the compliance as a relation between the first and second pluralities.

As mentioned above:
  the compliance determining means are preferably adapted to provide a relation between pairs of one of the first plurality of points in time or time intervals and one of the second plurality of points in time and/or
  the compliance determining means are preferably adapted to provide a relation between the pairs of one of the first plurality of points in time or time intervals and a first of the second plurality of points in time occurring after the pertaining point in time of the first plurality or within the pertaining time interval of the first plurality
  where the relation preferably then relates to a time difference between the pairs of the point in time or a starting time of the time interval of the first plurality and the point in time of the second interval.

Also, the compliance determining means are preferably adapted to provide a relation between a number of times wherein a point in time of the second number occurs within a time interval of the first plurality, and a number of times wherein a point in time of the second number does not occur within a time interval of the first plurality.

Again, the compliance determining means are preferably adapted to provide, as the information, one of a plurality of predetermined colours to the user, the colour being determined on the basis of the relation.

In addition, the compliance determining means may be adapted to provide, as the information:
  one of a plurality of predetermined numbers to the user, the number being determined on the basis of the relation,
  one or more of a plurality of predetermined areas of a display visible to the user, the area(s) activated being determined on the basis of the relation,
  one of a plurality of predetermined sound signals to the user, the sound signal being determined on the basis of the relation, and/or
  one of a plurality of predetermined graphical images to the user, the image being determined on the basis of the relation.

Also, means may be provided for informing the user, if a point in time of the second plurality occurs outside a time interval of the first plurality.

A third aspect of the invention relates to a medical dispenser being adapted to hold a number of medical doses, to inform a user or patient of when to take a dose, and to determine when the user or patient accesses a medical dose, the dispenser comprising:

means for informing the user in one of a plurality of different manners, means for, a number of times, operating the informing means in order to inform the user with different manners of informing, means for, during operation of the operating means, determining which manner(s) of informing brings the user or patient to access a medical dose, means for, subsequently to the operation of the operating means, selecting a manner of informing based on the determination.

Thus, the dispenser is adapted to select a manner of informing based on knowledge of which manner(s) brings the user or patient to actually access the medication.

Normally, the informing means would be adapted to inform the user using at least one of sound, visual information, or vibration. Preferably, the informing means are adapted to provide the sound, visual information, and/or vibration with different intensities and/or frequencies.

In a preferred embodiment, the determining means are adapted to determine that a manner of informing brings the user or operator to access a medical dose, when the user or operator accesses the dose while or within a predetermined period of time after the actual manner of operating is used. The predetermined period of time after the actual manner was used provides time for the user to react to the manner.

In order for the dispenser to determine which manner is e.g. the most efficient and in order to have the user take the medication, the operating means are preferably adapted to subsequently (one after the other) use different manners of information until the user gains access to a medical dose.

Not always will the user respond to the same manner of informing. This may be due to a number of reasons. Therefore, preferably, the selecting means are adapted to select a manner, which the most often brings the user or operator to gain access to the medical dose. This may be obtained when the operating means are adapted to be operated a plurality of times, the determining means being adapted to determine, for each of the plurality of times, which manner brings the user of operator to access the medical dose, and wherein the selecting means are adapted to select the manner having brought the user or operator the most often to access the medical dose.

A number of different dispenser types may advantageously use this technology, such as:

a dispenser being adapted to hold one or more blister cards holding the number of medical doses, and being adapted to detect that the user or patient has accessed a medical dose when the blister card is removed from the dispenser, a dispenser being adapted to provide one or more medical doses to the user or patient by inhalation, the dispenser having an air passage connected to a medical output and means for covering or closing the output or air passage when not in use, and being adapted to detect that the user or patient has accessed a medical dose when the covering means is removed from the dispenser, and/or a dispenser being adapted to provide one or more medical doses to the user or patient by injection by an injection needle, the dispenser having means for covering the injection needle when not in use, and being adapted to detect that the user or patient has accessed a medical dose when the covering means is removed from the dispenser.

It is interesting to note that the detecting means, informing means, etc. may, in fact, be positioned in the cover means in the injector/inhaler, so that standard injectors (such as an injector pen) or inhalers may be used and still gain the present functionality.

A fourth aspect of the invention relates to a medical dispenser being adapted to removably hold one or more blister cards for each holding a number of medical doses, and to inform a user or patient in relation to the taking of one or more medical doses, wherein:

the blister card comprises an indentation, a hole, or a protrusion at each of one or more of a plurality of predetermined positions, the dispenser having means for detecting an indentation, a hole, or a protrusion at each of the predetermined positions, and means for operating the informing means on the basis of an output from the detecting means.

Normally, a blister card is a square card without any indentations, holes or protrusions (apart from the blisters). The card may have rounded corners but will otherwise normally have straight sides.

Thus, the mechanical features (such as indentations, holes, protrusions) of the blister card are able to actually determine the operation of the dispenser. In this manner, the same dispenser may be used for different medications in that the medication when inserted will have the dispenser function correctly. Also, different manufacturers may "code" their blister cards differently in order to obtain different manners of operation of the dispenser.

In the context of the present invention, it should be noted that a blister card is a card holding a number of medical doses on or in a sheet-shaped (with blisters) member. Any form of sheet-shaped member may be used, and it is not required that the medication actually is present in blisters. The sheet-shaped member has advantages used in a number of the present embodiments in that it may be slid into and out of the dispenser and that it may have the mechanical features detected by detecting means in a number of the present embodiments.

Preferably, the detecting means has, at each of the predetermined positions, displaceable detecting means being displaced by a protrusion at the position of the blister card, or if no indentation or hole exists at the position. Such detecting means may operate on any of a wide variety of detecting schemes (mechanical, magnetic, optical detection, etc.)

The dispenser may be adapted to identify, from the positions of the blister card where indentations, holes, or protrusions are detected, one or more of:

a manufacturer of the medical doses, a type of medication in the medical doses, a frequency of recommended intake of the medical doses, recommended points in time of intake of the medical doses, a dose strength of one or more of the medical doses, and a manner of informing the user or operator (such as for reminder or compliance readout).

In a preferred embodiment, the dispenser further comprises means for determining a compliance of the user's or operator's intake of the medical doses based on:
- a predetermined medication schedule identified by indentations, holes, or protrusions or the lack of indentations, holes, or protrusions at predetermined positions of the blister card and
- information relating to points in time when the user or operator gains access to at least one of the doses of medication.

The identified medication schedule may be fully coded in the positions of the indentations etc, or may be stored in the dispenser and identified by e.g. a code or address coded in the positions of the indentations etc.

Preferably, the dispenser also comprises means for informing the user or operator to take a dose of the medication and means for determining when it is time to inform the user on the basis of:
- a predetermined medication schedule identified by indentations, holes, or protrusions or the lack of indentations, holes, or protrusions at predetermined positions of the blister card and
- a clocking device.

An interesting aspect is one where the dispenser being adapted to receive, from the user, information relating to:
- how to calculate compliance, and/or
- how to inform the user of compliance.

Thus, the user may himself set e.g. a compliance level which he desires to follow. The dispenser may then adapt its manners and times of informing—and may adapt a specific e.g. limit between levels of compliance (low, sufficient, high) so as to inform the user of his compliance in related to the selected compliance.

This information may be entered by the blister card(s) being adapted to have indentations, holes, or protrusions made subsequent to manufacture thereof, and wherein the dispenser is adapted to derive the information from the indentations, holes, or protrusions made subsequent to manufacture thereof. Thus, the user himself may provide the indentations etc. and thereby "code" the dispenser accordingly.

As mentioned above, the dispenser preferably comprises means for detecting or determining when the user or operator gains access to at least one of the medical doses.

Also, preferably, the dispenser comprises stationary means for introduction into further indentations at other positions of the blister card, the stationary means preventing a blister card not having the further indentations from engaging with the detecting means. In this manner, only blister cards having those further indentations will not be useable in the dispenser. This will prevent wrongful use of unoriginal blister cards in the dispenser.

In any of the above embodiments using a blister card, the dispenser may be able to hold the one or more blister card(s) in a manner so that the blister card is curved in a direction at least substantially along a longitudinal direction thereof. This curved state has a number of advantages in that the blister card is then biased against inner surfaces of the dispenser. A curved element (which in its rest position is straight) will obtain a much more stiff state across the direction of the bend. This may be used for a number of purposes, such as to maintain the blister card in the dispenser and to position the indentations etc. more precisely in the dispenser.

Preferably, the dispenser is adapted to receive the blister card(s), in a slot thereof, in a direction along the longitudinal direction of the blister card(s).

Preferably, the dispenser has a first surface and is adapted to bias an edge portion of each blister card being received thereby against the first surface. Then, the detecting means are preferably positioned a predetermined distance from the first surface and are able to detect the blister card(s) when positioned between the detecting means and the surface. The bent shape of the blister card will ensure that the positioning of the indentations etc is more precise.

A fifth aspect of the invention relates to a blister card for use in the dispenser according to the fourth aspect of the invention, the blister card has a number of blisters for each holding a medical dose, the blister card further comprising an indentation or a protrusion at each of one or more of a plurality of predetermined positions.

Normal blister cards have no protrusions, indentations or holes except for medicine blisters themselves and may be small mechanical features used for manipulating the blister cards during manufacture or packing.

Normally the present blister card is manufactured as a normal blister card with a subsequent step of providing the indentations etc. Optionally, protrusions may, in fact, be provided at the positions during providing of the blisters for the medication.

The blister card may also comprise further protrusions, holes, or indentations at the above-mentioned other positions in order to ensure that un-original blister cards are not used in the dispenser.

A sixth embodiment of the invention relates to a method of operating a medical dispenser being adapted to hold a number of medical doses and being adapted to determine when a user or patient gains access to one or more of the medical doses, the method comprising:
- determining each of a first plurality of points in time or time intervals at which the user or patient should take a medical dose,
- detecting each of a second plurality of points in time where the user or patient gained access to the medical doses, and
- providing to the user or patient information relating to a relation between the first and second pluralities.

As mentioned above, the providing step preferably comprises providing a relation between pairs of one of the first plurality of points in time or time intervals and one of the second plurality of points in time. Then, the providing step could comprise providing a relation between the pairs of one of the first plurality of points in time or time intervals and a first of the second plurality of points in time occurring after the pertaining point in time of the first plurality or within the pertaining time interval of the first plurality.

In one embodiment, the relation relates to a time difference between the pairs of the point in time or a starting time of the time interval of the first plurality and the point in time of the second interval.

In another embodiment, the providing step comprises providing a relation between a number of times wherein a point in time of the second number occurs within a time interval of the first plurality, and a number of times wherein a point in time of the second number does not occur within a time interval of the first plurality.

The providing step may comprise providing, as the information;
- one of a plurality of predetermined colours to the user, the colour being determined on the basis of the relation,
- one of a plurality of predetermined numbers to the user, the number being determined on the basis of the relation, one or more of a plurality of predetermined areas of a display visible to the user, the area(s) activated being determined on the basis of the relation, one of a plurality of predetermined sound signals to the user, the sound signal being determined on the basis of the relation, and/or one of a plurality of predetermined graphical images to the user, the image being determined on the basis of the relation.

Also, the method may further comprise the step of informing the user, if a point in time of the second plurality occurs outside a time interval of the first plurality.

A seventh aspect of the invention relates to a method of operating a medical dispenser being adapted to hold a number of medical doses, to inform the user in one of a plurality of different manners, and to inform a user or patient of when to take a dose, the method comprising:

determining a compliance of the user taking of medical doses, and selecting a manner of informing based on the determined compliance.

Thus, the informing step may comprise informing the user using one of sound, visual information, or vibration. Then, the determining step could comprise determining a compliance selected between a predetermined number of compliances, and the selecting means could be adapted to select visual information based on a first compliance of the predetermined number of compliances, vibration based on a second compliance of the predetermined number of compliances, and sound based on a third compliance of the predetermined number of compliances.

Also, the informing step could comprise providing the sound, visual information, or vibration with different intensities and/or frequencies. Then, the determining step could comprise determining a compliance selected between a predetermined number of compliances, and the selecting means could be adapted to select an intensity and/or frequency based on the determined compliance.

Preferably, dispenser is adapted to hold a number of medical doses and is adapted to determine when a user or patient gains access to one or more of the medical doses, the method comprising:

determining each of a first plurality of points in time or time intervals at which the user or patient should take a medical dose, and detecting each of a second plurality of points in time where the user or patient gained access to the medical doses, wherein the compliance determining step comprises determining the compliance as a relation between the first and second pluralities.

As mentioned above, the compliance determining step preferably comprises providing a relation between pairs of one of the first plurality of points in time or time intervals and one of the second plurality of points in time. Also, the compliance determining step could comprise providing a relation between the pairs of one of the first plurality of points in time or time intervals and a first of the second plurality of points in time occurring after the pertaining point in time of the first plurality or within the pertaining time interval of the first plurality.

Then, the relation could relate to a time difference between the pairs of the point in time or a starting time of the time interval of the first plurality and the point in time of the second interval.

Also, the compliance determining step could comprise providing a relation between a number of times wherein a point in time of the second number occurs within a time interval of the first plurality, and a number of times wherein a point in time of the second number does not occur within a time interval of the first plurality.

In any case, the compliance determining step preferably comprises providing, as the information:

one of a plurality of predetermined colours to the user, the colour being determined on the basis of the relation, one of a plurality of predetermined numbers to the user, the number being determined on the basis of the relation, one or more of a plurality of predetermined areas of a display visible to the user, the area(s) activated being determined on the basis of the relation, one of a plurality of predetermined sound signals to the user, the sound signal being determined on the basis of the relation, and/or one of a plurality of predetermined graphical images to the user, the image being determined on the basis of the relation.

The method preferably also comprises the step of informing the user, if a point in time of the second plurality occurs outside a time interval of the first plurality.

An eighth aspect of the invention relates to a method of operating a medical dispenser being adapted to hold a number of medical doses, to inform a user or patient of when to take a dose, inform the user in one of a plurality of different manners, and to determine when the user or patient accesses a medical dose, the method comprising:

a number of times, operating the informing means in order to inform the user with different manners of informing, during operation of the operating means, determining which manner(s) of informing brings the user or patient to access a medical dose, subsequently to the operation of the operating means, selecting a manner of informing based on the determination.

Preferably, the informing step comprises informing the user using one of sound, visual information, or vibration. Then, the informing step could comprise providing the sound, visual information, or vibration with different intensities and/or frequencies.

The determining step preferably comprise determining that a manner of informing brings the user or operator to access a medical dose, when the user or operator accesses the dose while or within a predetermined period of time after the actual manner of operating is used.

Also, preferably, the operating step comprises subsequently using different manners of information until the user gains access to a medical dose.

In the preferred embodiment, the selecting step comprises selecting a manner, which the most often brings the user or operator to gain access to the medical dose. Preferably, the operating step is operated a plurality of times, the determining step comprising determining, for each of the plurality of times, which manner brings the user of operator to access the medical dose, and wherein the selecting step comprises selecting the manner having brought the user or operator the most often to access the medical dose.

In a preferred embodiment of any of the sixth, seventh or eighth aspects, the method comprises the steps of the dispenser holding one or more blister cards holding the number of medical doses, and detecting that the user or patient has accessed a medical dose when the blister card is removed from the dispenser.

In another embodiment, the dispenser is adapted to provide one or more medical doses to the user or patient by inhalation, and the dispenser has an air passage connected to a medical output and means for covering or closing the output or air passage when not in use, the method comprising the step of detecting that the user or patient has accessed a medical dose when the covering/closing means is removed from the dispenser.

In a third embodiment, the dispenser is adapted to provide one or more medical doses to the user or patient by injection by an injection needle, and the dispenser has means for covering the injection needle when not in use, the method comprising the step of detecting that the user or patient has accessed a medical dose when the covering means is removed from the dispenser.

A ninth aspect of the invention relates to a method of operating a dispenser being adapted to removably hold one or more blister cards for each holding a number of medical doses, the blister card comprises an indentation, hole, or a protrusion at each of one or more of a plurality of predetermined positions, and to inform a user or patient in relation to the taking of one or more medical doses, the method comprising:

detecting, using detecting means of the dispenser, at each of the predetermined positions any indentation, hole, or a protrusion at that position, and
 operating the informing means on the basis of an output from the detecting means.

Then, the detecting step could comprise, at each of the predetermined positions having a protrusion or if no hole or indentation is present at the position, displacing a displaceable detecting means.

The method preferably comprises the step of identifying, from the positions of the blister card where indentations, holes, or protrusions are detected, one or more of:
 a manufacturer of the medical doses,
 a type of medication in the medical doses,
 a frequency of recommended intake of the medical doses,
 recommended points in time of intake of the medical doses,
 a dose strength of one or more of the medical doses, and
 a manner of informing the user or operator.

Also, the method may comprise the step of determining a compliance of the user's or operator's intake of the medical doses based on:
 a predetermined medication schedule identified by indentations, holes, or protrusions or the lack of indentations, holes, or protrusions at predetermined positions of the blister card and
 information relating to points in time when the user or operator gains access to at least one of the doses of medication.

Further, the method may comprise the steps of informing the user or operator to take a dose of the medication and of determining when it is time to inform the user on the basis of:
 a predetermined medication schedule identified by indentations, holes, or protrusions or the lack of indentations, holes, or protrusions at predetermined positions of the blister card and
 a clocking device.

In an interesting embodiment, the method comprises the step of the dispenser receiving, from the user, information relating to:
 how to calculate compliance, and/or
 how to inform the user of compliance.

Then, the blister card(s) may have indentations, holes, or protrusions made subsequent to manufacture thereof, and wherein the dispenser derives the information from the indentations, holes, or protrusions made subsequent to manufacture thereof.

Preferably, the method of this aspect further comprises the step of detecting or determining when the user or operator gains access to at least one of the medical doses.

In any of the embodiments of the sixth, seventh, eighth and ninth aspects incorporating a blister card, the method preferably comprises the step of the dispenser holding the one or more blister card(s) in a manner so that the blister card is curved in a direction at least substantially along a longitudinal direction thereof. Then, the method may comprise the dispenser receiving the blister card(s), in a slot thereof, in a direction along the longitudinal direction of the blister card(s).

The method also preferably comprises the step of biasing an edge portion of each received blister card against a first surface of the dispenser. Then, the detecting means could be positioned a predetermined distance from the first surface and detect the blister card(s) when positioned between the detecting means and the surface.

BRIEF DESCRIPTION OF THE DRAWINGS

In the following, preferred embodiments of the invention will be described with reference to the accompanying drawing, where FIG. 1A-1F illustrate a first preferred embodiment of a device according to the invention, and with means for monitoring the position of a blister card, FIG. 2A-2G illustrate a second embodiment of a device according to the invention, and with means for monitoring the position of a covering part, FIG. 3A-E illustrate a blister card and the use thereof, the blister card having holes, indentations or protrusions, FIG. 4A–4B are timelines showing possible ways of administering drugs utilising a device according to the invention.

DETAILED DESCRIPTION OF THE INVENTION

Figure 3C:
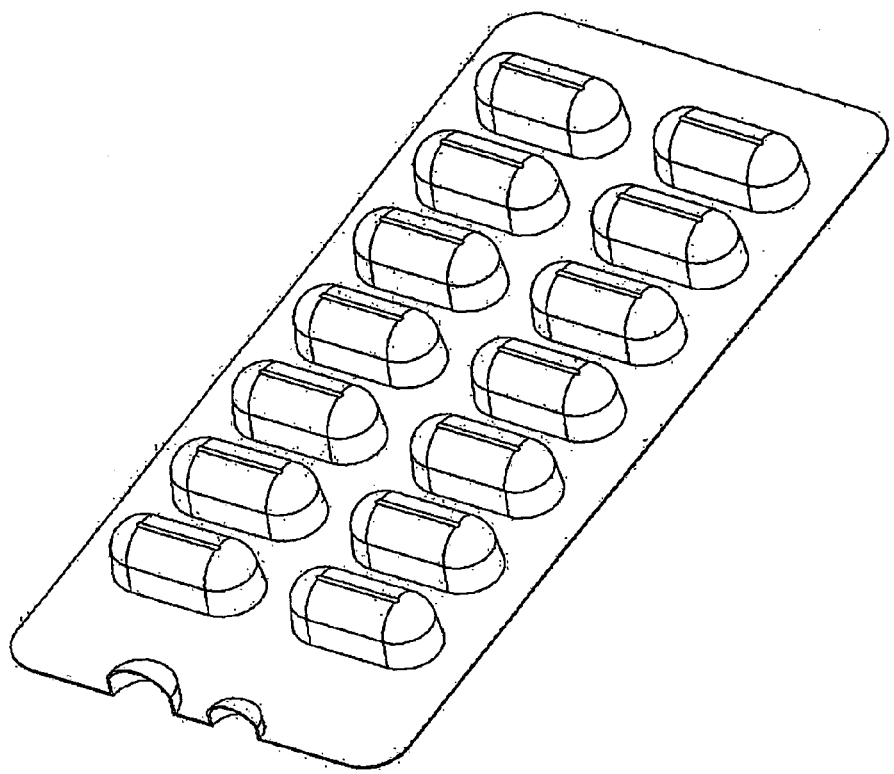
Figure 3D:
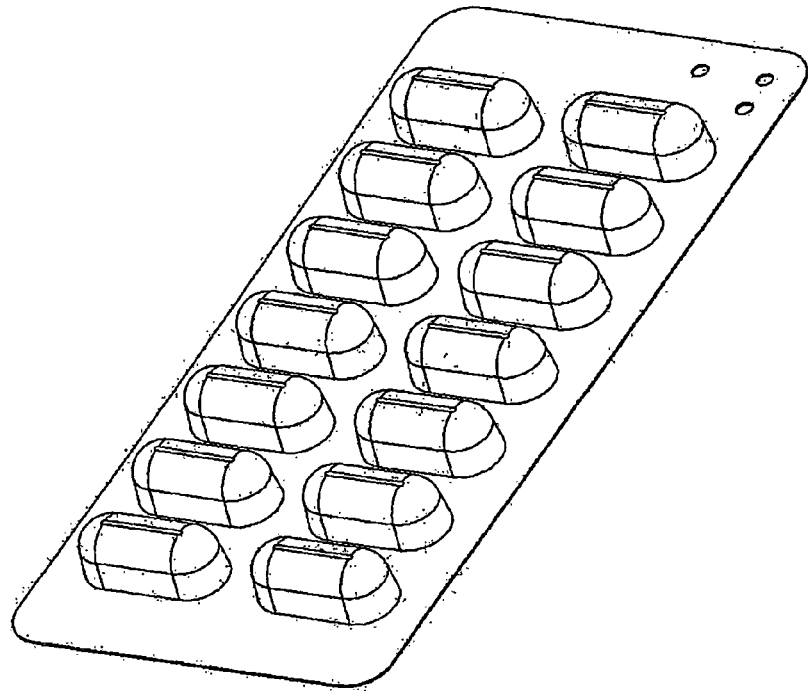

FIG. 1A-1F show a first embodiment of a device 1 for holding a blister card B. In FIG. 1F, the device is shown with a blister card B inserted into the device. The device 1 has a closed surface 2 and oppositely thereto a partly open surface 3. The partly open surface 3 has a slot 4 extending partly down the surface. The slot 4 is intended for inserting a finger for sliding the blister card B into and out of the device. The one end 5 of the device has an inlet 6 for inserting the blister card into and taking the blister card B out of the device. The other end of the device 1 has monitoring means (See FIG. 3) for registering the position of the blister card B.

The monitoring means is intended for registering a first position of the blister card B within the device, said first position being a position where the blister card is fully or almost fully inserted into the device (See FIG. 3B). Fully or almost fully inserted is a position where the closed surface 2 covers all of the tablets in the blister card B, so that not even one tablet can be taken from the blister card.

The monitoring means is preferably also intended for registering another position (See FIG. 3A) of the blister card B in relation to the device, said other position being a position where the blister card B is fully or partly pulled out of the device. Fully or partly pulled out is a position where the closed surface 2 does not cover the tablets T in the blister card B, or at least does not cover outer tablets in the blister card, so that at least one tablet can be taken.

In the embodiment shown the device also comprises a small signalling means 7 such as an LED or other lighting means placed in another end 8 of the device. The signalling means 7 may have different functions. The signalling means may be for signalling to the user when the blister card is in the first position or not, i.e. in the position, where tablets cannot be taken from the blister card.

The signalling means 7 may also be a means for reminding the user of when to take a tablet according to information from a dosage plan stored in an electronic memory (See FIG. 3) of the device. The signalling means 7 may also be a means for displaying to the user a level of compliance. A first level may be a level of compliance where the dosage of tablets to be taken and the time at which the tablets are to be taken have been fulfilled according to the dosage plan. In this situation, the signalling means 7 may show a steady green light. A second level of compliance may be a level of compliance, where the dosage of tablets to be taken and/or the time at which the tablets are to be taken, have not been fulfilled according to the dosage plan, but where satisfactory compliance still may be established if the dosage of tablets are taken now. In this situation the signalling means may show a steady yellow light. A third level of compliance may be a level of compliance where the dosage of tablets to be taken and/or the time at which the tablets are to be taken, have not been fulfilled according to the dosage plan, and where satisfactory compliance cannot be established, even if the dosage of tablets are taken now. In this situation, the signalling means may show a blinking red light, or a steady red light. Other ways of signalling may be established depending on other defined intermediate levels of compliance according to the information of dosage plan stored in the device.

The device is designed (See FIG. 1B) so that the closed surface 2 and the opposite surface 3 are curved. This has the advantage that when the blister card B is inserted through the inlet 6 into the device, the blister card B will be slightly bent compared to the planar configuration of the blister card B before insertion into the device. The slight bending of the blister card B will lead to the blister card B being wedged in the device, thereby holding the blister card B in the device without any elements as such for holding the blister card B within the device.

Thus, when the blister card B is inserted into the device through the inlet and is pushed all the way to the first position, where the blister card B is fully inserted in the device, the blister card B cannot drop out of the device. The curvature of the closed surface and the partly open surface 3 may have any rise H of the curvature in relation to a length of the blister card B. The only demand of the rise H of the curvature is that the blister card B must be so hardly wedged as not to drop out of the device by accident, perhaps when the inlet 6 of the device is directed downwards.

The device is also so designed that the one end 5 and the other end 6 of the device have flattened parts 9. The flattened parts 9 enable the placement of the device at a supporting surface such as a table. The device also has a shape and a size making it possible easily to bring the device along during the day, either in a bag, even a small lady's handbag, or in a pocket of a shirt or of a pair of trousers. The size of the device is not much larger than the size of the blister card B contained in the device. Thus, the device itself will not be limiting the compliance of the user, only the "discipline" of the user will determine the compliance.

Figure 2F:
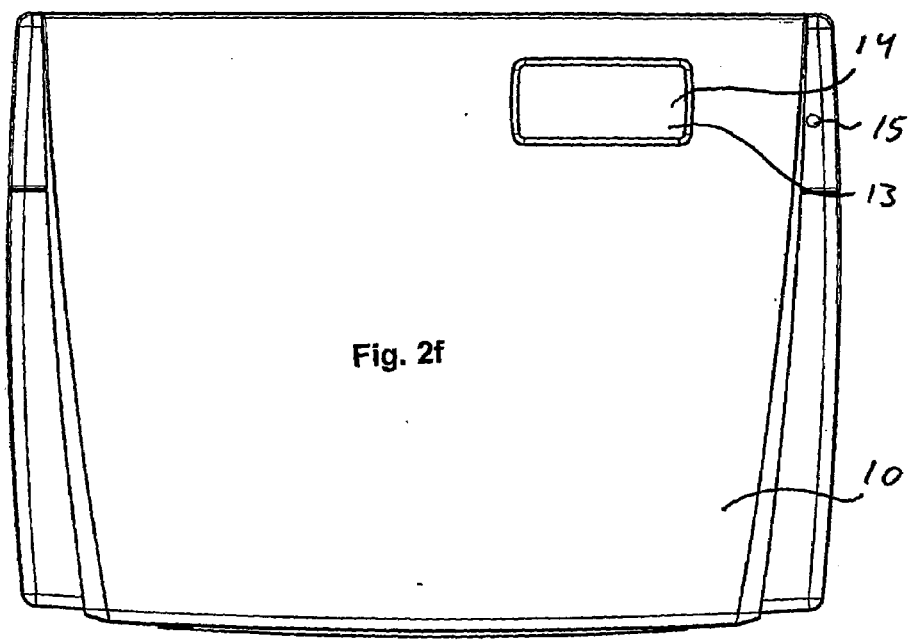
Figure 2G:
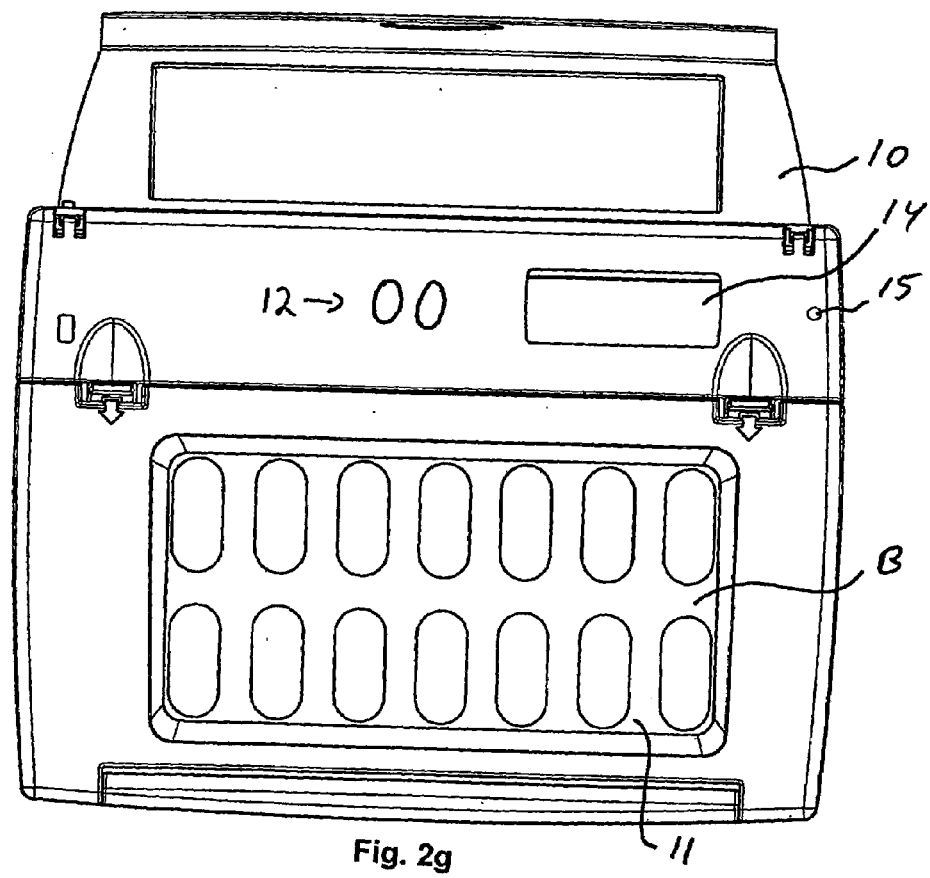

FIG. 2A-2G show a second embodiment of a device for holding a blister card B. In FIG. 2G, the device is shown with a blister card B inserted into the device. The device has a movable covering part 10; in the embodiment shown, a hinged covering part 10. In an alternative embodiment, the covering part 10 may be slidable along grooves in the device instead of being rotated as shown. In yet another embodiment, the covering part may just be liftable from a lowered closed state on top of the device to a raised open state separated from the device.

The covering part 10 is intended for covering a compartment 11 for holding the blister card B within the device. In an open state of the covering part 10, both the compartment 11 and control buttons 12 of the device are covered. In the embodiment shown, the covering part 10 has an aperture 13 for allowing viewing of a display 14, even if the covering part 10 is in the closed state. A small signalling means 15 is situated to the right of the covering part 10, and the covering part 10 does not cover this signalling means 15 either, even if the covering part 10 is in the closed state.

As mentioned above, in the embodiment shown the device also comprises a small signalling means 15 such as a LED or other lighting means such as the one shown in the first device of FIG. 1A-1F. The function and purpose of the signalling means 15 of the second embodiment shown in FIG. 2A-2G may be any one of the same purposes and functions as the ones described in relation to the first embodiment. Accordingly, the description related to the first embodiment of FIG. 1A-1F regarding the function and the purpose of the signalling means is hereby, by reference, incorporated into the description of the signalling means of the second embodiment shown in FIG. 2A-2G.

Apart from the signalling means 15, as mentioned, the second embodiment of the device also has a display 14. The display 14 may be used for many purposes and may include different functions. A display increases the amount of and the kind of information which may be given to the user apart from the information given by the previously described signalling means 15. Also, apart from the display 14, as mentioned, the second embodiment of the device has control buttons 12. Control buttons 12 may be used for different purposes. The control buttons 12 may be used for entering data into an electronic memory of the device. The control buttons may also be used for scrolling between different data or different sets of date, all capable of being shown in the display 14.

A bottom part 16 of the device shown in FIG. 2A-2G is provided with holes 17 intended as outlets for tablets from the blister card B contained in the compartment 11 of the device. The outlets 17 may have an orifice 18 planar with surface 19 of the bottom part 16. This will however necessitate holding the device in the hands of the user, when having to dispense one or more tablets from the blister pack in the compartment.

Therefore, in an alternative embodiment of the device, the outlets may have an orifice 18 being situated at a level above a level of the bottom surface 19. This leads to the advantage that the device may be placed at a supporting surface such as a table, when dispensing the tablets from the blister pack. In order for this function to be realised, the level at which the orifices of the outlets are situated must be situated above the level of the bottom surface in a distance being the same as or larger than a height of the tablets to be dispensed.

Thus, due to the possibility of orifices of the outlets situated in a plane above a level of the bottom surface, and thus above the supporting surface, there is room for the tablets between the orifice of the outlets and the supporting surface, when the device is placed with the bottom surface on the supporting surface. Being able to place the device on the supporting surface when dispensing the tablets, makes it very much easier to dispense the tablets from the blister pack, especially for elderly people or others having only a limited amount of strength in hands and fingers.

The bottom surface has a small cover (not illustrated). This cover is intended as cover for batteries for powering the signalling device, the display and any electronic memory storage means of the device. The batteries may also be used for powering possible means for transmitting data from the device or receiving data to the device from to a remote data receiving or data transmitting apparatus for storing, or in any other way handling data related to the usage and the monitoring facilities of the device.

The one side of the device has a plug 21. One or more plugs may be provided for different purposes. One purpose of a plug may be to provide the device with electrical power from an external power source, either as an alternative to the batteries, or as a supplement to the batteries. Another purpose of one or more plugs may be to provide the device with a wired link to an external data receiving and/or data transmitting apparatus. The number of plugs may also be intended for a telecommunication means such as modem or the like for providing the device with a wireless link to an external data receiving and/or data transmitting apparatus. Finally, the plug may be used for transmitting data to other devices related to the use of the device according to the invention, such other devices perhaps being a sound alarm, a lighting alarm or a tactile alarm in the vicinity of the device and of the user and having the purpose of alerting the user of when to take a tablet from the device in order to maintain or in order to obtain satisfactory compliance.

Monitoring the actual direct status of the dispenser and monitoring the compliance may take place by any suitable means. The display may, as shown in FIG. 2, constitute a part of the dispenser. However, alternatively the display may be connected to the dispenser either physically by a permanent or detachable wiring, or non-physically by means of wireless signals either to a separate display unit or perhaps to a mobile phone, or any other means of receiving wire-less signals.

Using wire-less signals to transmit the monitoring of compliance has the advantage that means for receiving messages that may be more frequently used than the dispenser, such as a mobile phone, will constitute the display means. This will increase the safety of the user taking the tablets at the prescribed times of drugs, and thereby maintain proper compliance. Furthermore, it will be possible for others than the user to monitor the compliance of the user, perhaps a doctor or other supervisor related to the dosage plan.

At least the device shown in FIG. 1, and possibly also the device shown in FIG. 2 may be provided with a mechanical switch which is engaged when a blister card B is stored in the device. Referring to the embodiment shown in FIG. 1, when the blister card B is removed from the first position, the switch is disengaged, this being monitored by a timer in the device. When the blister card B is moved to the first position again, the timer monitors this as a dosage of drugs having been taken.

In a possible functionally extended embodiment, the timer may-compute when the next dosage of drugs has to be taken according to a drug dosage plan, and the user may be reminded according to this drug dosage plan. When the switch is disengaged again, this is monitored as the blister card B having been removed from the first position, and compliance having been fulfilled if the removal complies with the drug dosage plan.

To avoid a user to achieve a misleading good compliance by pulling the card from and to the first position a number of times, the removal of the card could be registered as a tablet taken, only if it happens during an active alarm. This reduces the risk of a misleading compliance indication by failed operation, and makes it more cumbersome to cheat the device. This way of detecting the consumption of tablets is rather simple and inexpensive, but still relatively reliable and valuable as a new tool to optimise a treatment, and enable distinction between non-compliers and non-responders.

Referring to the embodiment shown in FIG. 2, the same functionality as above may be incorporated in a functionally extended embodiment. However, the monitoring is not a monitoring of a removal of the blister card B, but is a monitoring of lifting the covering part from the first and closed position to another and open position. In this way, exactly the same function as described above with reference to the embodiment of FIG. 1 may be obtained just by monitoring the covering part in stead.

Alternatively to a mechanical switch used for monitoring at least when the blister card B or the covering part is in the first position or not, other means of monitoring could be used. Thus, a capacitive monitoring may be used where the blister card B or the covering part introduces a change in a capacitor, when being placed in the first position compared to not being in the first position. Also magnetic means or optical means may be used to monitor when the blister card B or the covering part is in the first position or not. Additionally, seeing that the blister card B often have a back foil made of aluminium foil or perhaps another metal foil, electrical means sensing a conductivity of the foil of the blister card B may be used to monitor whether the blister card B is in the first position or not.

FIGS. 3A and B illustrate a dispenser 1 of the type illustrated in FIG. 1. The illustrated dispenser is flat but may also be curved as that of FIG. 1 in order to obtain the advantages thereof.

In FIG. 3A, the blister card B and the dispenser 1 are slightly separated in that the blister card B has been slided a little outwardly of the dispenser 1. In FIG. 3B, the blister card B is fully inserted into the dispenser 1.

The blister card B has two indentations or cut-away parts 40 which mate with corresponding protrusions 41 of the dispenser 1. These protrusions and indentations serve the purpose of preventing an unoriginal blister card from being fully inserted into the dispenser 1.

The reason for this may be seen in the detector 42, which, when the blister card B is fully inserted into the dispenser 1 (so that the indentations 40 and protrusions 41 mate) will be able to detect a feature of the blister card B at the position of the detector 42. Such a feature may be another indentation (not illustrated) as the indentations 40, a protrusion as is illustrated at 43 in FIG. 3C, or a hole as illustrated at 44 in FIG. 3D.

Figure 3E:
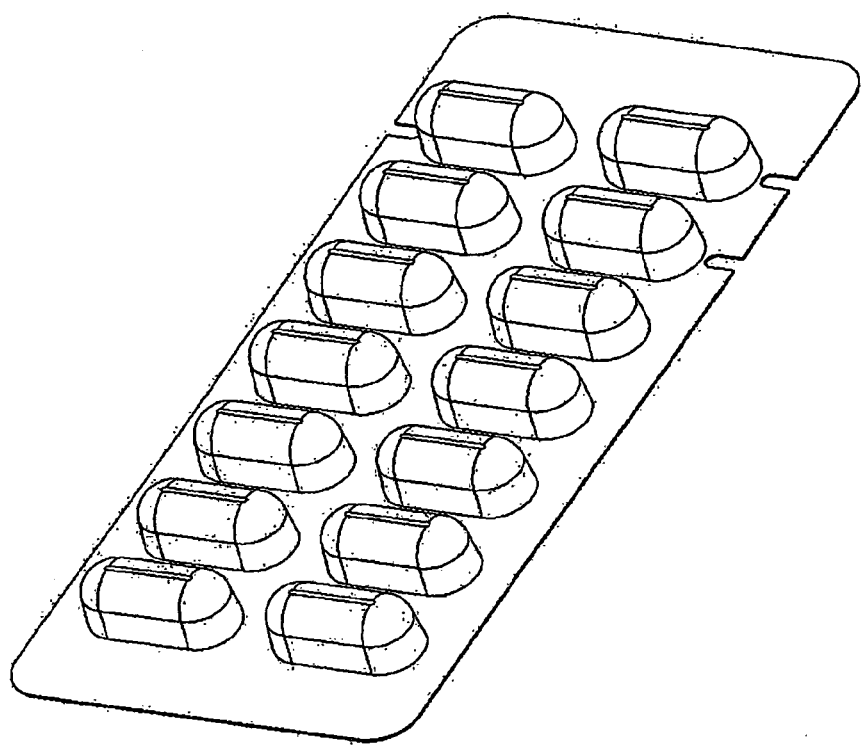

Another embodiment is indicated in FIG. 3E, where the indentations 46 (which may just as well be protrusions or holes) are positioned not at the bottom of the blister card B but at sides thereof so that a detector positioned in the slot receiving the card may be able to detect the features as the card is inserted—or when it is inserted.

Any number of detectors 42 may be used.

The detector may be based on optical, magnetical, or mechanical principles.

The dispenser 1 has electronics 45 to which the detector(s) 42 are coupled. These electronics furthermore comprise batteries, timer/clock, the reminding means (light emitter, vibrator, sound provider), a processor or CPU, and memory for storing data, such as medication schedules or programs for the CPU.

The features (40, 43, 44, 46) may be provided for informing the dispenser 1 of a number of different things, such as a manufacturer of the medical doses, a type of medication in the medical doses, expiration date of the medical doses, a frequency of recommended intake of the medical doses, recommended points in time of intake of the medical doses, a dose strength of one or more of the medical doses, a manner of informing the user or operator (which type of reminder does the user prefer for reminder and compliance readout) and What compliance level does the user himself wish to have (be informed of).

This information is detected (using the detector(s) 42) by the electronics 45 and may be used in the operation of the dispenser 1.

Thus, in fact, the user may himself provide indentations or other features in order to actually program the dispenser himself.

The blister card B may be provided from manufacture with score lines, weakenings, perforations or merely demarcations for providing such indentations for e.g. informing the electronics of the level of compliance to which the user wishes to be kept or which compliance levels should give which outputs by the dispenser 1 (see below).

Naturally, the blister card B would normally be provided with features from manufacture, such features informing the electronics of how the medical doses should be dispensed. Such features may be used for identifying one of a number of dispensing schemes kept in the memory of the electronics.

An optical fit as a recognising means between dispenser 1 and blister card B may be a an optically readable feature of the blister card B and a corresponding optical reader of the device, so that it is not possible at all to gather any information form the blister card B as to a dosage plan, if the optical reader of the device cannot read a corresponding optical readable feature of the blister card B. The optical fit may be correlated to perforations, a breaking off of a corner of the blister pack or the like physical entities of the blister card B, or the optical fit may be an optical entity such as a hologram, a certain printing, a bar code or the like. Perhaps the blister card B may be provided with a coding intended for a chosen drug dosage plan, said coding being selected by the user initial to introducing the blister card B in the device. One of a number of possible optical features fits may be indicative of the coding chosen by the patient, similarly to the more mechanical feature, where different levels of e.g. 85%, 90% and 95% compliance may be chosen, however optically by perhaps providing a hole at a chosen location of the blister card B, and a corresponding reader such as a photo cell provided in the device. In FIG. 3, a feature is used for electronic/mechanical coding, however similarly, the photo cell recognising light through a hole in the blister card B may be used for optical coding.

Any coding of the blister card B itself may be directly related to the drugs, the number of tablets contained in the blister card B and other conditions which are essential for proper and correct drug administration of the drugs in the blister card B in question.

An embodiment and functionality as the one described above, where the blister card B is provided with encoding may be beneficial for a manufacturer of drugs in blister cards B, because the manufacturer before handing over to the user the drugs in the blister card B can be sure of the encoding ensuring a proper compliance if complied with. Thus, the manufacturer does not have to rely on a doctor or other exterior medical personnel coding the device with the risk of wrongful coding of the device.

As mentioned, perhaps the encoding of the blister card B may be made by means of visually or electronically readable and tamper-proof means such as a hologram, a perforation or a small electronic circuit resembling or in any other way utilising trademarks solely used by the manufacturer. Thereby, it will be not be possible to use drugs and blister cards from other manufacturers. Also, the user can be sure that the drugs in the blister card B and the encoding with a drug dosage plan are mutually compatible, and that the drugs, if taken according to the drug dosage plan, will ensure proper compliance according to the prescribed manufacturer of the drugs. Even alternatively, the blister card B may be provided a special design only used by the manufacturer, and having the same purpose of individualisation as described above.

Also as mentioned, another alternative way of implementing variable compliance targets for the users would be to implement the break-off tabs on the blister card B itself. This means that the device is manufactured to reward a certain compliance. After a while, the user can set higher targets by breaking off tabs, which will cause the device to give rewards at a higher level of compliance.

All the devices shown may have one or more signalling means capable of reminding the user of taking the drugs either by a visual, an audible or a tactile signal. The visual signal is a lamp lighting red or other colour, when the time for delivering the drugs arises. The audible signal may be a siren sounding a warning-like signal. The siren may be adjustable, both in relation to the sound level and in relation to the sound produced. The sound produced may also differ depending on when the drugs is taken along a time interval after the time of delivering has been reached. At the beginning of the time interval, after the time of delivering has been passed, the audible sound is "pleasant" and/or at a low level. As long as the drugs is not taken and depending on how long time after the time of delivering that the drugs is still not taken, then the audible sound will be less "pleasant", i.e. it will start being more alert-like or alarm-like, and/or the audible sound level will increase either stepwise or gradually. The sound may be a beeping sound or it may be a recording of a voice or an exclamation.

Such an adaptive reminding could also be implemented with visual alarming means, such as light emitting diodes, where a flashing pattern changes over time, as the interval since the start of the alarm gets longer. The light produced may also differ depending on when the drugs is taken along a time interval after the time of delivering has been reached. At the beginning of the time interval, after the time of delivering has been passed, the light could be a flashing green light, different from a steady green light, or an alternating green and yellow flashing.

As long as the drugs is not taken and depending on how long time after the time of delivering that the drugs is still not taken, then the light could change to alternating yellow and red flashing and further to a constant and steady red light perhaps even to a flashing red light. The light could be a single light with the above-mentioned pattern of alarming, or it could be a plurality of lights each having their distinct colour and either not lighting or lighting steadily or flashing depending on the level of compliance at a certain time, either during or after the drugs should have been taken according to a drug dosage plan stored in a memory of the device. If the device, as shown in FIG. 2, is provided with a display, the level of compliance may also or in stead be displayed by for example a percentage.

Alternatively, a display may be used for informing the user of his/her compliance in the form of a number, a pictogram (happy/sad face) or other manners which will lead the user to know his/her compliance.

In the latter case, either a voice or an exclamation, the sound may be added some humour or a command-like tone so that the sound is personalised in relation to the user utilising the device for taking drugs. By personalising the sound, then the initiative for taking the drugs may be increased. If the sound is a voice it may be the voice of a doctor, preferably the user himself or the user's own doctor, motivating the user to take the drugs, and the command being more and more harsh along with the drugs not being taken after the time of delivering has been exceeded. If the sound is added humour it may be one exclamation at the beginning of the time interval, after the time of delivering has been exceeded, and being another exclamation late in the time interval if the drugs are still not taken.

Any personalised voice and command or any personalised exclamation which the user chooses will add to the personalising of the device, and thus to impel to handle the device and the taking of the drugs seriously. Such sounds could also be attached to the achieved compliance, so that a good compliance causes a positive or rewarding sound to be played and a poor compliance causes a motivating sound to be played.

Compliance may be determined in a number of manners, and the user may, e.g., select a specific manner by providing a feature of the blister card B. Compliance may be determined as how long after the optimum time (as defined by e.g. a medication schedule) the user actually takes the medication. Alternatively, time may be divided into intervals, and the compliance may be determined as the frequency at which the user takes the medication in a given interval or after a predetermined period of time after the optimum point in time.

Compliance may be determined as a mean over a period of time depending on e.g. a feature of the blister card B or depending on the type of medication. For some types of medication, compliance should be determined over a time interval of at least a month, and for others, a few days would suffice.

The specific manner of informing the user that it is time to take a dose of medication may vary with the users present compliance. If the user is compliant to the medication scheme, a pleasant manner of informing the user may be selected, whereas a non-compliant user may be informed in a less pleasant manner. More pleasant manners may be the emission of light, a light vibration of a pleasant sound, whereas less pleasant manners may be more aggressive vibration and/or sounds.

Another situation where different manners of informing the user may be relevant is one where the dispenser determines that a given manner of informing the user has no effect or that a given manner has a particularly high effect. A situation of that type would be to rule out audio information for a user who turns out to be deaf of light or vibration information when the dispenser is normally placed in a hand bag.

Thus, the dispenser may be able to test different manners of informing and to determine which manners are the most useful—and to thereafter predominantly use these. The determination of whether a manner of informing is useful may be made on the basis of whether the user takes the medication during or shortly after that manner of informing has been used.

FIG. 4A-B shows how drugs could be administered with a device according to the invention, and it visualizes the different administration rules a device is capable of supporting. Basically, a prescription of medicine for example from a doctor to a patient comprises a specification of a drug to be taken and an ideal dosage of the drug to be taken at a certain moment of time, or within a certain time interval. The dosage is related to a certain dosage of drugs (e.g. two tablets) with a certain interval (for example every 24 hours). Therefore the administration is related to a calendar (100), where a number of ideal dosages (110) should be taken at a certain moment of time during the day or within a certain time interval during the day.

In the example shown, the patient is supposed to take one tablet every day at 8 AM. If this administration scheme is followed precisely, the patient compliance is at a maximum. Deviations from the ideal scheme can be interpreted as varying lack of, or a decreased level of compliance. The purpose of the device according to the present invention is to monitor this compliance by application of different rules dependent on the actual function of the relevant drug. Further, the purpose of the device according to the invention is to improve the compliance, both by providing the patient with information about the actual level of compliance and by reminding the patient when to take the drug in order to maintain a certain level of compliance.

The total time can by way of example be subdivided into two main categories, described in the following. Allowed periods (117): The patient is allowed to take a dosage. The period starts at or before the ideal dosage time or reminding time. It seizes when a dosage is taken, when all previous dosages have been taken, or when the next ideal dosage is close-by. Prohibited periods (118): The patient is not allowed to take a dosage. The purpose of the prohibited periods is to avoid over-dosage or to avoid risky high drug concentrations within the patient. The prohibited period starts when a dosage is taken, when the right average dosages have been reached, or when the next ideal dosage is close-by. It seizes when a new ideal dosage is close-by. These periods can be divided into a number of relevant sub-periods for more detailed monitoring information.

For example, this more detailed information could be: Early intake (125), ideal intake (126), delayed intake (127), intake prohibited (caused by dosage taking), next dosage prohibited (128) etc. The number and the kind of sub-periods depends on the therapy, the kind and amount of drug and on the patients, and might be related to any relevant information in relation to timing of dosages or use of the device.

The term "allowed" and the term "prohibited" refer to periods of time of a drug dosage plan. Allowed is when drug intake according to the drug dosage plan is recommended, i.e. where drug dosage should take place in order to obtain a certain state or a certain level of compliance according to the drug dosage plan. Prohibited is when drug intake according to the drug dosage plan is not recommended, i.e. where drug dosage, if taking place, perhaps will lead to overdosage, or where drug dosage, if taking place, perhaps will lead to an incorrect follow-up of the drug dosage plan, and a non-existent possibility of reestablishment of compliance according to the drug dosage plan.

The allowed and prohibited periods (117, 118) are the default status of the device. However, dependent on the patient's interaction with the device, the device can change its actual status. For example, the prohibited period (130) is initiated by the device activation (131), as the device is trying to make the patient follow the rule that tablets should not be taken too close to each other in order to avoid too high drug concentration, i.e. a over-dosage. The prohibited period (135) is initiated by the default status, as the dosage was not taken in the allowed period and the next alarm is approaching. The device activation (136) is therefore causing a warning signal (121).

The device can be programmed with the dosage information and can therefore remind the patient at or linked to the ideal dosage time. This is done by a reminder or an alarm (120), which informs the patient that it is time to take the prescribed dosage. An alarm can continue to be activated until a dosage is taken, or it can be cancelled or changed from an audio signal to a visual signal after a certain period of time. In the example shown, the alarm is cancelled either by an activation of the device (blister card B is taken out or the covering of the device is lifted), or because the allowed period ends and the device enters a prohibited period, where dosage taking is not recommended, because the next alarm is coming soon. If the device is activated in a prohibited period, the device could give the patient an acoustical warning signal (121, 122, 123) indicating that it is not recommended to take a dosage.

Dependent on the function of the drug taken, different rules for administration can be relevant. Events that influence the way of administration could for example be the time before the active substance in the tablet is transferred from the tablet to the blood, the time before the active substance is influencing the relevant site in the body, the half-time period of the active substance etc. If the consequences of a high concentration of drugs within the patient is harmless and/or the half-time period is longer than the period between taking of drug dosages, the timing is relative uncritical, and good compliance is achieved by taking, in average, the acquired number of dosages. For example, it may be acceptable to take two dosages at the same time if the previous dosage was forgotten. A device for such drug could therefore add up the number of reminders, so that previously forgotten dosages still are reminded to the patient.

For drugs with a very critical upper limit of active substance concentration, for example drugs for anticoagulation treatment, other rulers might be implemented in the device. In this example, the device will give the patient a warning if a dosage is taken too close to the previous dosage taken, or too close to the next ideal dosage to be taken.

Figure 6:
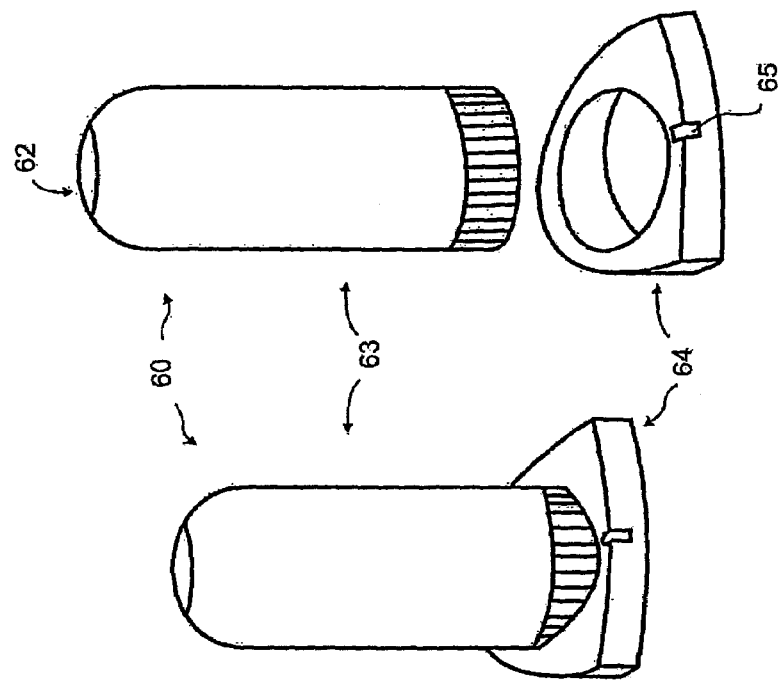
FIG. 6 illustrates an embodiment of the invention use in an inhaler.
Figure 5:
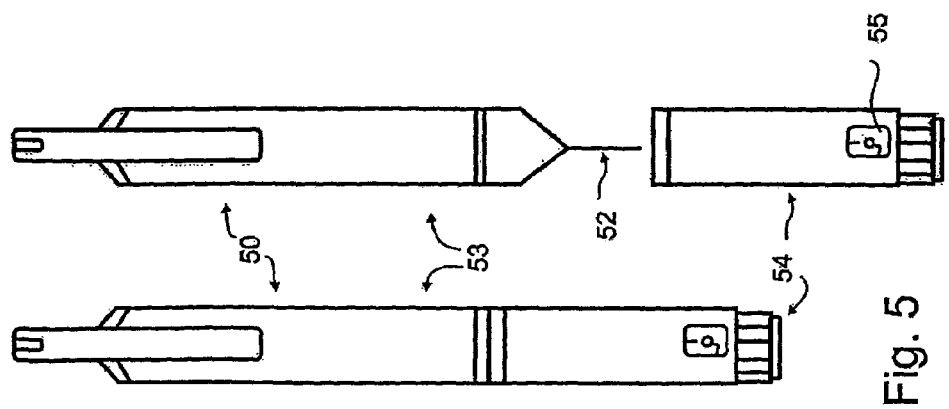
FIG. 5 illustrates an embodiment of the invention used in an injector.

FIGS. 5 and 6 illustrate other embodiments than pill dispensers holding blister cards.

In FIG. 5, the dispenser is an injection pen 50 having a syringe 52 for injection of medication present in a first part 53 of the pen 50. When not in use, the syringe 52 is not in use, it is covered by a cover 54 which comprises the detecting means, CPU, memory, informing means, providing means etc (in general denoted 55) desired to obtain the desired functionality according to the invention.

In this manner, no changes are required for the pen 50 in order to obtain the desired functionality.

Thus, when removing the cover 54 in order to gain access to a medication dose, the detecting means (54) will detect that, and the dispenser 50 act accordingly.

FIG. 6 illustrates another embodiment having an in hater. The dispenser 60 has the inhaler 63 having a medication output 62 for the user to inhale through, and a base 63. The inhaler has an air passage passing through the output 62 and a bottom of the inhaler. This bottom is blocked by the base 63, when the inhaler 63 is not in use and positioned in the base 63.

As is the case for the pen of FIG. 5, the base 63 of the inhaler comprises all means and functionalities required (denoted 65>) in order to gain the advantages of the present invention. Again, no changes are required in the actual inhaler 63.

In this aspect, it should be noted that even further manners of delivery may be altered in order to obtain the advantages of the invention: nasal sprays, transdermal deliveries, rectal delivery, etc.

The invention claim is:

1. A medical dispenser being adapted to hold a number of medical doses and being adapted to determine when a user or patient gains access to one or more of the medical doses, the dispenser comprising:
    means for determining each of a first plurality of points in time or time intervals at which the user or patient should take a medical dose,
    means for detecting each of a second plurality of points in time where the user or patient gained access to the medical doses,
    means for providing to the user or patient information relating to a relation between the first and second pluralities, and
wherein the providing means are adapted to, if the user gains access to the medication multiple times per point in time or time interval in the first plurality of points in time or time intervals, provide information relating to a relation between the pairs of
    one of the firs plurality of points in time or time intervals and
    a first of the second plurality of points in time occurring after the pertaining point in time of the first plurality or within time interval of the first plurality.

2. A medical dispenser according to claim 1, wherein the relation relates to a time difference between the pairs of the point in time or a starting time of the time interval of the first plurality and the point in time of the second interval.

3. A medical dispenser according to claim 1, wherein the providing means are adapted to provide a relation between a number of times wherein a point in time of the second number occurs within a time interval of the first plurality, and a number of times wherein a point in time of the second number does not occur within a time interval of the first plurality.

4. A medical dispenser according to claim 1, wherein the providing means are adapted to provide, as the information, at least one of a group consisting of
    a plurality of predetermined colours to the user, the colour being determined on the basis of the relation,
    a plurality of predetermined numbers to the user, the number being determined on the basis of the relation,
    one or more of a plurality of predetermined areas of a display visible to the user, the area(s) activated being determined on the basis of the relation,
    one of a plurality of predetermined sound signals to the user, the sound signal being determined on the basis of the relation, and one of a plurality of predetermined graphical images to the user, the image being determined on the basis of the relation.

5. A medical dispenser according to claim 1, further comprising means for informing the user, if a point in time of the second plurality occurs outside a time interval of the first plurality.

6. A method of operating a medical dispenser being adapted to hold a number of medical doses and being adapted to determine when a user or patient gains access to one or more of the medical doses, the method comprising:

determining each of a first plurality of times or time intervals at which the user or patient should take a medical dose, detecting each of a second plurality of points in time where the user or patient gained access to the medial doses, providing to the user or patient information relating to a relation between the first and second pluralities, and wherein the providing step comprises, if the user gains access to the medication multiple times per point in time or time interval in the first plurality of points in time or time intervals, providing information relating to a relation between the pairs of one of the first plurality of points in time or time intervals and a first of the second plurality of points in time occurring after the pertaining point in time of the first plurality or within the pertaining time interval of the first plurality.

7. A method according to claim 6, wherein the relation relates to a time difference between the pairs of the point in time or a starting time of the time interval of the first plurality and the point in time of the second interval.

8. A method according to claim 6, wherein the providing step comprises providing a relation between a number of times wherein a point in time of the second number occurs within a time interval of the first plurality, and a number of times wherein a point in time of the second number does not occur within a time interval of the first plurality.

9. A method according to claim 6, wherein the providing step comprises providing, as the information, one of the group consisting of one of a plurality of predetermined colours to the user, the colour being determined on the basis of the relation.

one of a plurality of predetermined numbers to the user, the number being determined on the basis of the relation.

one or more of a plurality of predetermined areas of a display visible to the user, the area(s) activated being determined on the basis of the relation.

one of plurality of predetermined sound signals to the user, the sound signal being determined on the basis of the relation.

one of a plurality of predetermined graphical images to the user, the image being determined on the basis of the relation.

10. A method according to claim 6, further comprising the step of informing the user, if a point in time of the second plurality occurs outside a time interval of the first plurality.

* * * * *